United States Patent [19]

Dalton

[11] Patent Number: 4,632,671
[45] Date of Patent: *Dec. 30, 1986

[54] CONDUIT ANCHOR ADAPTED TO RECEIVE STYLET

[76] Inventor: Michael J. Dalton, 9432 Monticello Ave., Evanston, Ill. 60203

[ * ] Notice: The portion of the term of this patent subsequent to Aug. 7, 2001 has been disclaimed.

[21] Appl. No.: 722,329

[22] Filed: Apr. 12, 1985

[51] Int. Cl.⁴ .............................................. A61M 5/32
[52] U.S. Cl. ...................... 604/174; 604/51; 604/167; 604/180; 128/DIG. 26
[58] Field of Search .................. 128/DIG. 26, 133; 604/8, 93, 9, 164–167, 170, 115, 174–185, 274, 51

[56] References Cited

U.S. PATENT DOCUMENTS

| | | | |
|---|---|---|---|
| 3,487,837 | 1/1970 | Petersen | 604/180 |
| 3,765,414 | 10/1973 | Arlen | 128/260 |
| 3,951,147 | 4/1976 | Tucker et al. | 604/891 |
| 4,080,970 | 3/1978 | Miller | 604/174 |
| 4,133,312 | 1/1979 | Burd | 604/8 |
| 4,177,814 | 12/1979 | Krepshield | 604/167 |
| 4,190,048 | 2/1980 | Sampson | 604/175 |
| 4,318,401 | 3/1982 | Zimmerman | 604/51 |
| 4,464,178 | 8/1984 | Dalton | 604/174 |

FOREIGN PATENT DOCUMENTS

| | | | |
|---|---|---|---|
| 2901302 | 7/1980 | Fed. Rep. of Germany | 604/180 |
| 0920028 | 3/1963 | United Kingdom | 604/175 |

Primary Examiner—C. Fred Rosenbaum
Assistant Examiner—Mario Costantino
Attorney, Agent, or Firm—Richard L. Hansen

[57] ABSTRACT

This invention is an improvement in an anchor for a transcutaneous conduit, such as a hypodermic needle, used in conjunction with a subcutaneous reservoir having a conduit-penetrable septum. The anchor includes a resilient protective boot having a plurality of concentric annular rings stacked using the conduit as an axis, beginning with a base ring carrying adhesive for attachment to the skin of a living body and ending with a terminal ring to be attached to the conduit, and includes means, when the terminal ring is attached to the conduit, to urge the protective boot into a compressed state along the axis and the conduit into the body. The improvement provides means for inserting a stylet into the anchor and through the conduit to prevent coring the septum when the conduit is inserted into the reservoir.

10 Claims, 6 Drawing Figures

CONDUIT ANCHOR ADAPTED TO RECEIVE STYLET

This invention is in the field of means for introducing or removing fluid from the body for therapeutic purposes using a transcutaneous conduit; more particularly, the invention is directed to means employed to secure the conduit to the body.

It is known in the art to implant a fluid receptacle beneath the skin to act as a depot or reservoir to accumulate material to be transferred to or from a remote site in the body, e.g., through a catheter connecting the reservoir with the site. Fluid is typically added to the reservoir or withdrawn from the body by means of a transcutaneous conduit, such as a hypodermic needle. The conduit typically is inserted into the reservoir through a penetrable septum which reseals itself upon withdrawal of the conduit. When treatment requires that fluid be added or withdrawn frequently over an extended period of time it is desirable to leave a transcutaneous conduit in place, rather than repeatedly puncture the skin.

Further, in order to minimize the possibility of dislodgement, and for the comfort of the patient, such semi-permanent transcutaneous conduit is preferably affixed very securely to the surface of the body. An anchor for such a fluid delivery conduit is described in my U.S. Pat. No. 4,464,178. The current invention is an improvement of that anchor.

In certain cases, such as in the treatment of peritoneal diseases, ovarian cancers and the like, as well as in the peritoneal dialysis employed in treating end stage renal disease, it is necessary to transfer large volumes of fluid through the conduit rapidly. This requires that the lumen of the conduit be large, e.g., 16 or 18 gauge. When a conduit having a large lumen is inserted into the septum of the subcutaneous reservoir there is a risk that the conduit will cut a core out of the septum, destroy its ability to reseal, and cause fluid to leak into the tissue surrounding the reservoir. This can present a serious problem, especially if the fluid is a cytotoxic drug.

It is to this problem that the instant invention is directed. This invention addresses the problem by providing means for inserting a stylet or obturator into the anchor and through the conduit. The conduit-stylet combination can then be pushed through the septum of the subcutaneous reservoir without coring it and the stylet then withdrawn.

The invention will be clarified upon reference to the drawings, which illustrate preferred embodiments, and to the detailed description which follows.

Figure 1:
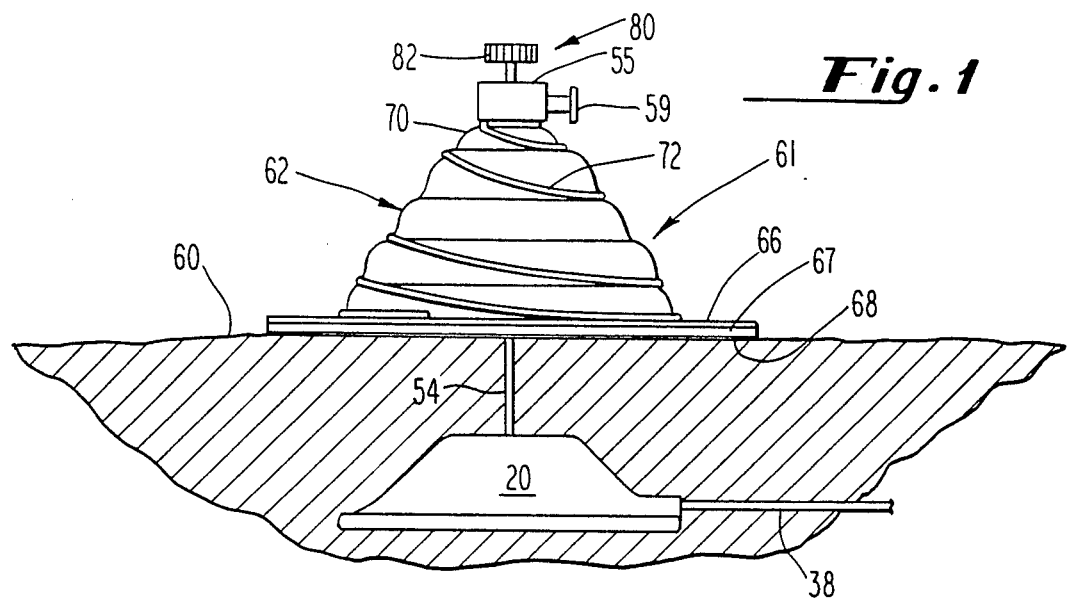
FIG. 1 is a side elevation showing the conduit anchor of this invention and its relationship to a transcutaneous conduit and subcutaneous reservoir.

Referring first to FIG. 1, anchor 61, which is above the surface of skin 60 and includes protective boot 62, secures conduit 54 to the body. Conduit 54 may be mated to coupling 55, as described hereinafter, and thence to a supply of the fluid. Conduit 54 penetrates a resilient septum in implanted reservoir 20, and catheter 38 connects the reservoir with the site of treatment. Using means provided by this invention, a stylet 80 may be inserted into the protective boot and through conduit 54.

Figure 2:
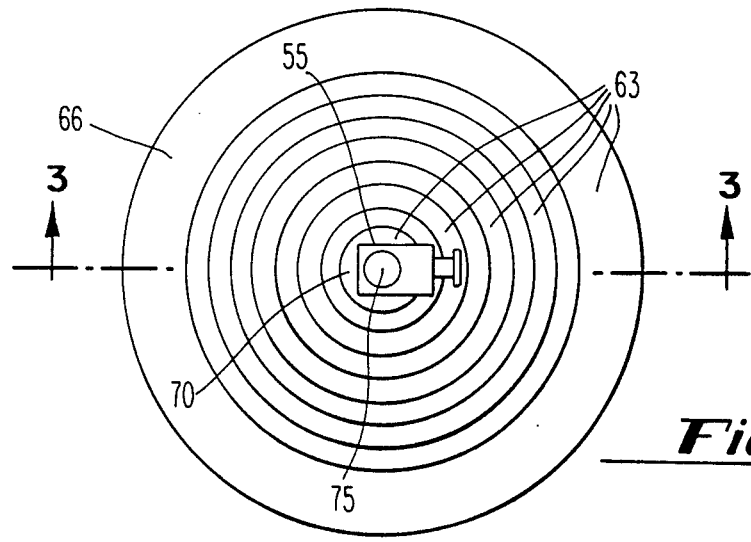
FIG. 2 is a top plan view of a conduit anchor according to this invention.

Protective boot 62 is shown in a somewhat extended position in FIG. 1, with conduit 54 as its axis. As seen in FIG. 2, the protective boot includes a plurality of connected concentric annular rings 63, beginning with base ring 66 adapted for attachment to the skin and ending with terminal ring 70, which may be attached to coupling 55. The protective boot is reilient so as to extend and compress along the axis of conduit 54, but is tensioned, for example, using helical spring 72, to remain compressed, thereby urging compression of protective boot 62 and forcing fluid delivery conduit 54 into reservoir 20, while providing a shock-absorbing construction and a sealed environment about the wound in the skin.

Protective boot 62 is a resilient construction, conveniently injection molded from a plastic material, for example, a polyolefin such as polypropylene about 0.025 cm thick, but base ring 66 may be thicker, to about 0.05 cm, to impart lateral stiffness. When it is produced by molding, the protective boot should be molded with terminal ring 70 compressed toward base ring 66, thereby providing a restoring set, urging compression of the protective boot along the conduit axis to minimize its vertical profile and, when the protective boot is joined to conduit 54, urging the conduit into the implanted reservoir.

Protective boot 62 may be joined to conduit 54 in several ways. The conduit may be attached to coupling 55. Terminal ring 70 can be connected to coupling 55 by any of a number of techniques, including solvent or adhesive bonding and ultrasonic welding, but coupling 55 may also be formed as part of the protective boot. Terminal ring 70 may also be attached directly to conduit 54. Regardless of the manner by which protective boot 62 and conduit 54 are joined, means are provided to insert a stylet into the anchor and through the hollow conduit. Such means include simply constructing the boot of a material, such as polyolefin, which can be punctured by the stylet. Preferably, however, means such as a resilient, penetrable, resealable septum, e.g., rubber, are provided in the anchor to reseal upon removal of the stylet, so as to preserve the integrity of the anchor. If the protective boot is attached to coupling 55, it is convenient to affix such a septum in the coupling, e.g. in the coupling wall using an appropriate adhesive, e.g., silicone.

Figure 3:
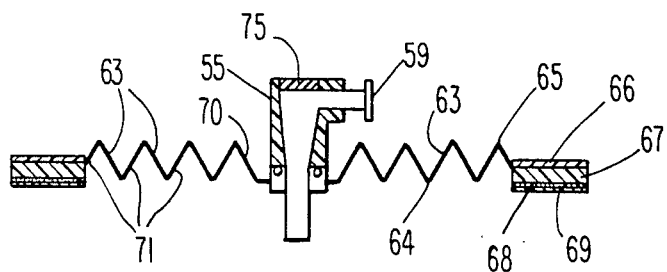
FIG. 3 is a cross-sectional view taken along line 3—3 in FIG. 2.

The conduit anchor is illustrated in greater detail in FIGS. 3–6. With reference to FIG. 3, protective boot 62 is shown in a compressed state. Each annular ring 63 has an inside periphery 64 and an outside periphery 65. In this embodiment the rings are of progressively smaller outside periphery diameter from base ring 66 to terminal ring 70, attached to coupling 55. Septum 75 provides access to the coupling interior and thence to an attached conduit. Each annular ring is flexibly joined by inter-ring connection 71 to the next adjacent ring alternately at inside and outside peripheries. Base ring 66 carries a medically acceptable adhesive, such as a pressure-sensitive adhesive, for attachment to the patient's skin. For maximum comfort it may be desirable to interpose cushion layer 67, which may be a foam, such as polyurethane foam, between base ring 66 and adhesive layer 68. The exposed adhesive may be protected with removable coating or liner 69 until the conduit anchor is readied for use.

In general, it is preferred to maintain the vertical profile of the conduit anchor as low as possible, for example by urging the protective boot into a compressed state. This may be accomplished, for example, in molding the protective boot and/or by employing spring means 72 as described above. The anchor profile can also be decreased by molding conduit 54 with coupling 55 in one piece, thereby avoiding the need for coupling member 57, on one end of conduit 54, and part of coupling 55. Alternatively, or additionally, the need for coupling 55 can be avoided altogether by extending conduit 54 to a releasable fitting mounted elsewhere on the protective boot; for example, on base ring 66. Thus, it will be evident that apparatus equivalent to that which includes coupling member 57 and coupling 55, as illustrated herein, is achieved by omitting these elements, thereby providing apparatus in which, for example, terminal ring 70 is attached directly to conduit 54.

Figure 4:
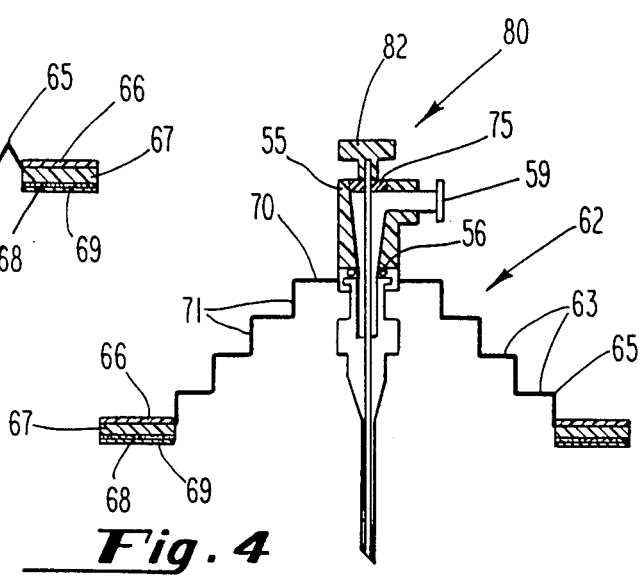
FIG. 4 is a cross-sectional view like FIG. 3, but showing the anchor in an extended position and illustrating a fluid delivery conduit and a stylet in relation to the conduit anchor.

FIG. 4 illustrates the conduit anchor of FIGS. 2 and 3, but with protective boot 62 in an extended state, showing annular rings 63 stacked using conduit 54 as the axis. FIG. 4 also shows the conical shape of the protective boot when the annular rings are of progressively smaller outside periphery diameters from the base ring to the terminal ring. Connection of fluid conduit 54, by means of coupling member 57, to coupling 55, and thence by connection 59 to a supply of the fluid, is also shown in FIG. 4. A stylet 80, which includes sharpened wire 81 and retainer 82, is shown inserted into septum 75 and through conduit 54.

As illustrated, coupling 55 is a 90 degree male/female Luer lock-type fitting, but any releasable, fluid tight fitting will suffice; for example, the screw or bayonet types. If Luer lock couplings, well known in the art, are used, O ring 56 may be employed to decrease the probability of a fluid leak.

Figure 5:
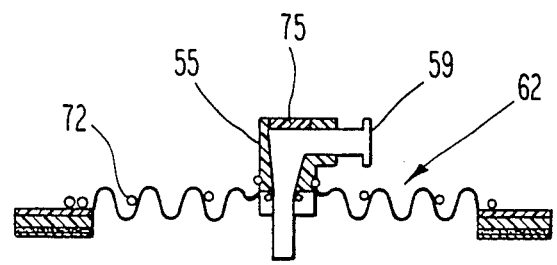
FIGS. 5 and 6 are cross-sectional views like FIGS. 3 and 4, but illustrating other embodiments of the conduit anchor.

In the embodiment shown in FIGS. 2–4, each annular ring is substantially flat between its inside and outside peripheries. FIG. 5 illustrates an alternative embodiment wherein each annular ring, other than the base ring, is S-shaped between its inside and outside peripheries. In FIG. 5 protective boot 62 is shown in a compressed state; this type of boot is shown in extended form in FIG. 1. Spring means 72, illustrated in FIGS. 1 and 5 only, is an optional feature which can be employed with any of the conduit anchors of this invention.

Figure 6:
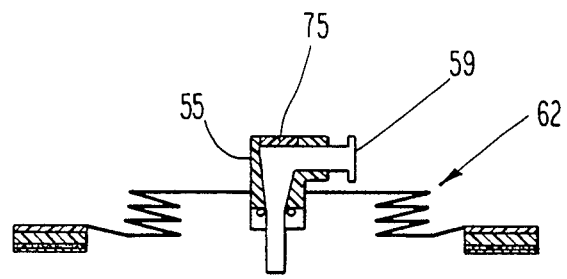

Another embodiment of the conduit anchor appears in FIG. 6, wherein the annular rings, other than the base ring, have the same outside periphery diameter. The protective boot of FIG. 6 describes a cylinder when extended.

It will be evident that a number of variations can be made in protective boot 62, in the means provided for inserting a stylet into the protective boot and through conduit 54, and in the other details of this invention, while remaining within the scope of the following claims.

What is claimed is:

1. In an anchor for an elongated hollow transcutaneous fluid delivery conduit which includes a resilient protective boot having a plurality of concentric annular rings with inside and outside peripheries and stacked using said conduit as an axis beginning with a base ring carrying adhesive for attachment to the skin of a living body and ending with a terminal ring to be attached to said conduit, each ring in said stack being flexibly connected to the next adjacent ring alternately at said inside and outside peripheries to provide shock-absorbing extension and compression along said axis, and including means, when said terminal ring is attached to said conduit, to urge said protective boot into a compressed state along said axis and said conduit into said body, the improvement therein which comprises providing a penetrable resealable septum in said anchor for inserting a stylet into said anchor and through said hollow conduit.

2. The anchor of claim 1 wherein said terminal ring is attached to a coupling which can be joined to said conduit and said septum is affixed in said coupling to allow for stylet insertion into said conduit.

3. The anchor of claim 2 wherein said coupling is a 90 degree releasable male/female fitting.

4. A transcutaneous fluid delivery system which comprises:
   (a) a fluid receptacle for subcutaneous surgical implantation in a living body, said receptacle including fluid inlet and outlet means;
   (b) an elongated hollow fluid delivery conduit adapted at one end for supercutaneous connection to a supply of the fluid, an other end thereof being adapted for subcutaneous penetration of said receptacle; together with
   (c) an anchor for securing said conduit on the body which includes a resilient protective boot having a plurality of concentric annular rings with inside and outside peripheries and stacked using said conduit as an axis beginning with a base ring carrying adhesive for attachment to the skin of the body and ending with a terminal ring to be attached to said conduit, each ring in said stack being flexibly connected to the next adjacent ring alternately at said inside and outside peripheries to provide shock-absorbing extension and compression along said axis, and including means, when said terminal ring is attached to said conduit, to urge said protective boot into a compressed state along said axis and said conduit into said body, together with a penetrable resealable septum in said anchor for inserting a stylet into said anchor and through said hollow conduit.

5. The fluid delivery system of claim 4 wherein said terminal ring of said anchor is attached to a coupling which can be joined to said conduit and said septum is affixed in said coupling to allow for stylet insertion into said conduit.

6. The fluid delivery system of claim 5 wherein said coupling is a 90 degree releasable male/female fitting.

7. A method for the long-term delivery of a therapeutic fluid to selected sites within a living body which comprises:
   (a) implanting a fluid receptacle in the body, said receptacle having fluid inlet and outlet means;
   (b) penetrating said receptacle with one end of an elongated hollow fluid delivery conduit adapted at an other end thereof for supercutaneous connection to a supply of the fluid;
   (c) securing said conduit on the body with an anchor which includes a resilient protective boot having a plurality of concentric annular rings with inside and outside peripheries and stacked using said conduit as an axis beginning with a base ring carrying adhesive for attachment to the skin of the body and ending with a terminal ring to be attached to said conduit, each ring in said stack being flexibly connected to the next adjacent ring alternately at said inside and outside peripheries to provide shock-absorbing extension and compression along said axis, and including means, when said terminal ring is attached to said conduit, to urge said protective boot into a compressed state along said axis and said conduit into said body, together with a penetrable resealable septum in said anchor for inserting a stylet into said anchor and through said hollow conduit.

8. The method of claim 7 wherein said terminal ring of said anchor is attached to a coupling which can be joined to said conduit and said septum is affixed in said coupling to allow for stylet insertion into said conduit.

9. The method of claim 8 wherein said coupling is a 90 degree male/female fitting.

10. The method of claim 7 which further comprises inserting a stylet into said anchor and through said hollow conduit prior to penetrating said receptacle.

* * * * *